United States Patent
Bendtsen et al.

(10) Patent No.: US 11,903,609 B2
(45) Date of Patent: Feb. 20, 2024

(54) METHOD FOR PREPARING AN INSERTION SITE FOR A CANNULA ON A SKIN OF A PATIENT, A SKIN COVER UNIT THEREFORE AND ITS USE

(71) Applicant: US Enovacor ApS, Ebeltoft (DK)

(72) Inventors: Thomas Fichtner Bendtsen, Aarhus (DK); Erik Sloth, Risskov (DK); Lars Knudsen, Risskov (DK); Neal Joseph Buchalter, Short Hills, NJ (US)

(73) Assignee: US ENOVACOR APS, Ebeltoft (DK)

( * ) Notice: Subject to any disclaimer, the term of this patent is extended or adjusted under 35 U.S.C. 154(b) by 46 days.

(21) Appl. No.: 16/964,249

(22) PCT Filed: Jan. 25, 2019

(86) PCT No.: PCT/DK2019/050032
§ 371 (c)(1),
(2) Date: Jul. 23, 2020

(87) PCT Pub. No.: WO2019/145009
PCT Pub. Date: Aug. 1, 2019

(65) Prior Publication Data
US 2021/0038249 A1  Feb. 11, 2021

Related U.S. Application Data
(60) Provisional application No. 62/621,651, filed on Jan. 25, 2018.

(30) Foreign Application Priority Data
Feb. 12, 2018  (DK) .......................... PA 2018 70085

(51) Int. Cl.
*A61B 17/34* (2006.01)
*A61B 8/08* (2006.01)
(Continued)

(52) U.S. Cl.
CPC ........ *A61B 17/3403* (2013.01); *A61B 8/0841* (2013.01); *A61F 13/023* (2013.01);
(Continued)

(58) Field of Classification Search
CPC .............. A61B 17/3403; A61B 8/0841; A61B 2017/00924; A61B 2017/3413;
(Continued)

(56) References Cited

U.S. PATENT DOCUMENTS 5,702,356 A    12/1997  Hathman
9,393,381 B2 *  7/2016  Sloth ..................... A61M 25/02
(Continued)

FOREIGN PATENT DOCUMENTS

EP    1702642 A1   9/2006
EP    2394600 A1  12/2011
(Continued)

*Primary Examiner* — Sean D Mattson
*Assistant Examiner* — Michael Yiming Fang
(74) *Attorney, Agent, or Firm* — Cermak Nakajima & McGowan LLP; James Creighton Wray

(57) ABSTRACT

An insertion site for a cannula (23) on a skin (8) of a patient is prepared by applying a skin cover unit (1) of the type comprising a window (2) and a wall (3) in extension of the window (2) and connected to the window (2) by a bending region (4) for bending the wall (3) into an angled orientation relatively to the window (2); wherein the win-dow (2) comprises a stabilizing frame (5) and an ultrasonic-transparent flexible sheet (6) within the frame (5). The flexible sheet (6) is glued onto the skin (8) of the patient for ultrasonic investigation of the insertion site through the flexible sheet (6). By bending the bending region (4), the angular orientation of the wall (3) is adjusted into an approximately perpendicular orientation relatively to the window (2) for separating the insertion site from the flexible sheet (6) by the wall (3). The cover unit (1) in or at the
(Continued)

bending region (4) comprises a stabilizer (9) that is configured for maintaining the angled orientation between the wall (3) and the window (2) by a stabilizing action of the stabilizer (9).

11 Claims, 8 Drawing Sheets

(51) Int. Cl.
    *A61F 13/02* (2006.01)
    *A61M 25/02* (2006.01)
    *A61B 17/00* (2006.01)

(52) U.S. Cl.
    CPC ............... *A61B 2017/00924* (2013.01); *A61B 2017/3413* (2013.01); *A61M 2025/0273* (2013.01)

(58) Field of Classification Search
    CPC ............ A61B 90/04; A61B 2017/3407; A61B 8/4281; A61B 8/00; A61F 13/023; A61F 2013/00412; A61F 2013/00182; A61F 13/00; A61M 2025/0273; A61M 25/02; A61M 2025/0266; A61M 25/01
    See application file for complete search history.

(56) References Cited

U.S. PATENT DOCUMENTS

| | | | |
|---|---|---|---|
| 2004/0138602 A1* | 7/2004 | Rossen | A61F 13/0226 602/41 |
| 2005/0215953 A1* | 9/2005 | Rossen | A61M 25/02 604/180 |
| 2006/0207609 A1 | 9/2006 | Gil | |
| 2013/0281904 A1* | 10/2013 | Jackson | A61F 13/023 602/42 |
| 2013/0289404 A1 | 10/2013 | Sloth | |
| 2014/0073899 A1 | 3/2014 | Cohrs | |
| 2014/0135629 A1 | 5/2014 | Hoppmann | |

FOREIGN PATENT DOCUMENTS

| | | |
|---|---|---|
| WO | 02085233 A1 | 10/2002 |
| WO | 2004041064 A2 | 5/2004 |

* cited by examiner

METHOD FOR PREPARING AN INSERTION SITE FOR A CANNULA ON A SKIN OF A PATIENT, A SKIN COVER UNIT THEREFORE AND ITS USE

This application claims the benefit of U.S. Provisional Application 62/621,651 filed Jan. 25, 2018, Danish Application No. PA 2018 70085 filed Feb. 12, 2018 and PCT/DK2019/050032 filed Jan. 25, 2019, International Publication No. WO 2019/145009 A1, which are hereby incorporated by reference in their entirety as if fully set forth herein.

FIELD OF THE INVENTION

The present invention relates to an ultrasonic-transparent surgical skin cover unit for use when inserting a puncture device, such as a cannula, electrode or probe, into a human body, for example into a vein or artery. The present invention relates in particular to procedures involving an ultrasonic device for visualisation of the exact location for the puncturing with the puncture device.

BACKGROUND OF THE INVENTION

When a cannula is inserted into a part of a body, for example a blood vessel of an arm or leg, the insertion can be optimized by visualising the blood vessel and the cannula using ultrasonic visualization.

U.S. Pat. No. 9,393,381 and the corresponding patent application US2013/0289404 disclose a skin cover unit for this purpose. The skin cover unit comprises an ultrasonic-transparent window, made of polymer film, which is glued onto the skin adjacent to the puncture site and onto which an ultrasonic probe is placed for imaging the puncture site during insertion of the cannula. Typically, for better contact between the ultrasonic probe and the polymer film of the window, a gel is used between the probe and the film. In order to properly separate the probe from the puncturing site and for preventing gel to flow to the puncturing site, an upstanding wall is provided in extension of the window, separating the window from the puncturing site. The film for the window is relatively stiff and enables an upstanding wall to be in an position upright to the window. Optionally, the unit comprises a gel-removing layer on top of the window for removing the gel-removing layer together with the gel from the window after ultrasonic visualization.

Although, the principle as disclosed in the application US2013/0289404 appears theoretically sound, it does not work properly in practice. This is so because a film stiff enough to hold the wall upright does have a tendency to not readily attach closely to the skin of the patient with the consequence of inferior ultrasonic transmission. On the other hand, making the film flexible enough for good skin contact and proper ultrasonic transmission implies a tendency of the upstanding wall not being sufficiently stabilized in upright position. In practice, it has turned out that this upstanding wall is structurally stable only if the skin cover unit is placed on arms and legs where the skin is curved in a direction parallel to the wall. However, if the skin cover unit is used on flat skin areas, the upstanding wall is not standing by itself but has to be held manually in place. This is a disadvantage, as the skin cover unit is not working optimally in this situation.

DESCRIPTION/SUMMARY OF THE INVENTION

It is therefore an objective of the invention to provide an improvement in the art, in particular an improved skin cover unit for ultrasonic-assisted control when inserting a cannula or other puncture device at a puncturing site on the skin, for example for injection or blood draws. This objective is achieved with a surgical skin cover unit and its use as explained in greater detail in the following.

The skin cover unit comprises a window and a wall in extension of the window and connected to the window by a bending region for bending the wall into an angled orientation relatively to the window. The window comprises an ultrasonic-transparent flexible sheet that covers an ultrasonic-transparent part of the window, typically flexible polymer film.

Optionally the window comprises a stabilizing but also flexible frame, within which the flexible sheet is provided. The flexible sheets is attached to and supported by the frame. For example, the material of the frame is thicker and more mechanically stable and rigid than the flexible sheet. The stable frame allows the ultrasound-transparent sheet being provided thin and flexible for bending easily with the skin and rest tightly against the skin for good ultrasound transmission, why such a stable frame is an advantage.

On a first side of window, for example on one side of the frame, there is provided an adhesive layer for gluing the window onto the skin of a patient. The opposite, second side of the window is configured for contact with the ultrasonic probe for visualization of the insertion area adjacent to the window when inserting a cannula into the skin.

Typically, the wall is made of a polymer film, paper sheet, or a dressing textile or a combination thereof. For transport, typically, the wall is provided in longitudinal extension of the window, such that the window and wall are packed in straight flat condition. Alternatively, the window and wall are folded onto each other into a compact double layer configuration which has to be unfolded for use.

When the skin cover unit is unpacked from a package, the wall is folded into an angled, typically perpendicular or largely perpendicular orientation, relatively to the window in order to provide the wall in upstanding orientation relatively to the skin. This folding is done before or after gluing the window onto the skin.

As an improvement relatively to the above-mentioned U.S. Pat. No. 9,393,381, the cover unit, in addition to the ultrasonic-transparent flexible sheet, comprises a stabilizer that is configured for maintaining the angled orientation, for example perpendicular orientation, between the wall and the window by a stabilizing action of the stabilizer.

For example, the stabilizer is positioned outside the ultrasonic-transparent part of the window. Optionally, the stabilizer or part of the stabilizer is positioned along a perimeter of the ultrasonic-transparent part of the window. This is contrast to the aforementioned US2013/0289404, where the ultrasonic-transparent film itself is used for stabilizing and therefore has to be stiff, which is disadvantageous, as the film should be smoothly and easily flexible in order to readily follow the contour of the skin for proper ultrasound transmission into the skin.

For example, if a frame is provided as part of the window, the stabilizer is provided on the frame and on the wall for stabilizing the orientation of the wall relatively to the frame.

Advantageously, the stabilizer is provided in or at the bending region, which typically is the region where the wall is connected to the window. For example, the stabilizer is in itself bendable so that the window and wall can be manually bent about the bending region from a planar or collapsed configuration into a bent configuration where the wall is angled relatively to the window, for example angled perpendicular to the window. However, once the wall is bent relatively to the window into the angled orientation, for example perpendicular orientation, the stabilizer maintains the angled orientation between the wall and the window. Typically, the bending of the wall relatively to the window about the bending region is along a bending line.

For example, the stabilizer is non-resiliently bendable and configured for adopting and maintaining a selectable bending condition when being bent for thereby maintaining a selected orientation of the wall relatively to the window. When the non-resiliently stabilizer is bent into the selected bent configuration it maintains this bent configuration. For example, the stabilizer comprises a metal foil with non-resilient bending properties. Optionally, the stabilizer is provided as a non-resiliently bendable hinge, for example a non-resilient bendable polymer sheet or metal foil, that is adopting and maintaining a selectable bending condition when being bent for thereby maintaining a selected orientation of the wall relatively to the window.

For example, the stabilizer is bent into a collapsed double-layer configuration during manufacturing and supplied in the collapsed position where the window is abutting the wall. It is then partially un-bent in use. Alternatively, the stabilizer is not bent during manufacturing and supplied in the non-bent configuration, typically straight configuration, which is then bent for use.

In some embodiments, the stabilizer is provided as a bendable sheet comprising a first part that is fastened to the wall. In extension of the first part of the bendable sheet, the bendable sheet comprises a second part, which comprises an adhesive layer for fastening the bendable sheet to the second side of the window, once the wall is bent relatively to the window. Alternatively, the first part of the bendable sheet is fastened to the second side of the window, which is the side that is facing away from the skin when in use, and the second part is configured with adhesive for attachment to the wall, once the wall is bent relatively to the window.

Typically, the bendable sheet is provided with only the first part fastened to the wall or window from the onset and is fastened manually to the other part by adhesive after bending, as already described in the foregoing.

In some embodiments, the first stabilizer part is fastened to the wall and the second stabilizer part comprises a portion at an edge of the wall for fastening the portion to the frame of the window. For example, the first stabilizer part is fastened to the wall and the second stabilizer part comprises a portion at each of two opposite edges of the wall, and the method comprises fastening the two portions to two opposite parts of the frame of the window.

In other embodiments, the stabilizer is already fastened to both the window and the wall and acts as a non-resilient hinge which keeps its bent condition after bending.

In some embodiments, the stabilizer is configured for, after fastening, maintaining a distance between at least two points remote from bending region, thus forming a stable triangular configuration between the two points and the bending region. For example, the stabilizer is fastened to a first point on the wall and a second point on the frame, both points being at a distance remote from the bending region.

In some embodiments, the wall comprises a slot extending from an edge of the wall towards the window. In some embodiments, a slit is provided in the wall material, and the slot can then be provided by pressing apart the two adjacent opposite edges of the slit. Alternatively, the slot is provided with a suitable width to ease insertion of the cannula. In this case, the wall comprises a first wall side with an adhesive for also gluing the wall to the skin of the patient and for locating the cannula inside the slot while the wall is glued to the skin of the patient. The adhesive of the first wall side is covered by a cover layer. This gives some options for use as explained in more detail in the following.

For example, the cover layer is kept on the adhesive of the first wall side while it is used as an upstanding wall adjacent to the insertion site, while the wall is bent relatively to the window. Selectively, the cover layer is then removed from the adhesive and the wall glued to the patient's skin after insertion of the cannula in order to accommodate the cannula inside the slot after gluing. Alternatively, the cover layer of the adhesive on the wall is removed together with the cover layer of the adhesive of the window, and the wall and window are glued onto the skin of the patient before ultrasonic investigation.

In some embodiments, the ultrasonic-transparent flexible sheet, for example polymer film, is glued to the skin with an adhesive that provides a good contact for ultrasonic transmission from the flexible sheet and into the skin. However, this is not strictly necessary.

For example, if the sheet is made of a thin polymer film, the film itself may readily attach to the skin and follow the contour of the skim even without glue. The principle is similar to the attachment properties of kitchen wrap film. However, for such thin and flexible film, a stable frame is an advantage in that the stable frame gives the necessary stability for not only holding the film but also the wall, and the film can be made sufficiently thin for good skin contact.

In order to provide a good contact between the ultrasonic probe and the flexible sheet of the window it is often advantageous to use an ultrasonic fluid, typically a gel. This gel is applied to the ultrasonic-transparent flexible sheet prior to the ultrasonic investigation and then removed again. For example, the gel is wiped off after use of the ultrasonic probe. Alternatively, a gel-removal strip, which is also ultrasonic transparent, is provided on top of the flexible sheet and forms part of the window. This gel-removal strip is then taken off and removed from the ultrasonic-transparent flexible sheet together with the gel such that wiping off the gel from the window is avoided. For example, the gel-removal strip extends under at least part of the stabilizer, for example under the entire stabilizer, for by manual removal of the gel-removal strip from the flexible sheet also removing the stabilizer.

Examples of suitable materials for the components of the skin cover unit are

Frame: woven, knitted or non-woven fabric, or plastic, rubber, paper, silicone, or combinations thereof.

Ultrasonic-transparent flexible sheet: rubber, paper, silicone, or plastics, or combinations thereof; for example including polyurethane or elastomeric polyesters (PolyEthylene Terephthalate—PET).

Wall: plastic, rubber, paper, silicone, woven, knitted or non-woven fabric, or combinations thereof.

Stabilizer: Polyester (PolyEthylene Terephthalate—PET), Polyethylene, Polyamide (Nylon), paper (typically coated) or combinations thereof.

The ultrasonic-transparent flexible sheet is to be understood as a sheet that comprises elasticity and resiliency for the sheet to be able to follow the movements of the skin and remain attached. For example, the flexible sheet has a thickness in the range of 10-45 microns.

Non-limiting but typical examples of dimensions are as follows:

Width: 4-10 cm
Length: 7.5 cm to 15 cm
Thickness for each layer: 10 to 45 microns.

Although the invention has been exemplified by insertion of a cannula as the puncture device, it applies equally well in the case of insertion of a different type of puncture device, for example an electrode for nerve stimulation or a transducer for recording electric signals from nerves. A further use of the skin cover unit is insertion of a probe for analysis of chemical agents, for example oxygen, metabolites, or drugs.

SHORT DESCRIPTION OF THE DRAWINGS

The invention will be explained in more detail with reference to the drawing, where FIG. 1 illustrates a bent skin cover unit as a) a drawing of a first embodiment, b) a principle sketch, c) drawing of a second embodiment, and d) a drawing of a third embodiment;

Figure 5A:
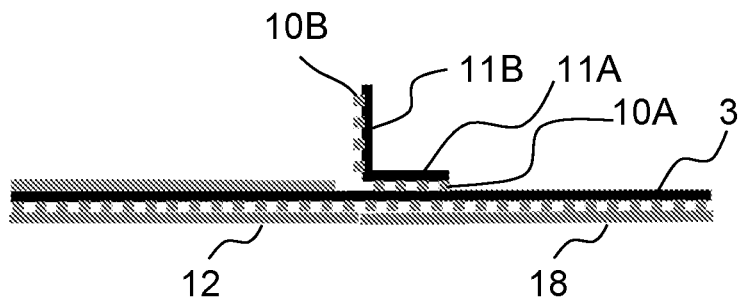
Figure 5B:
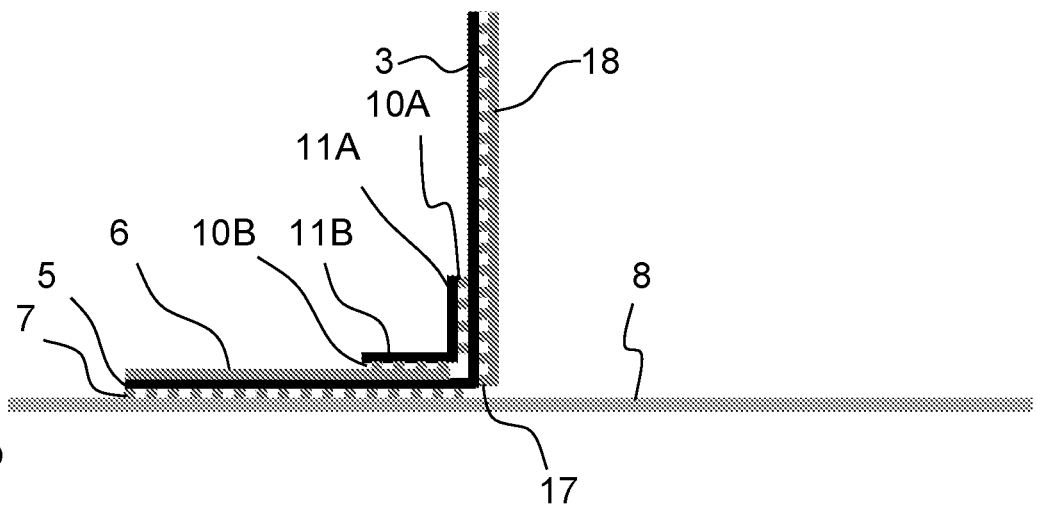
Figure 6:
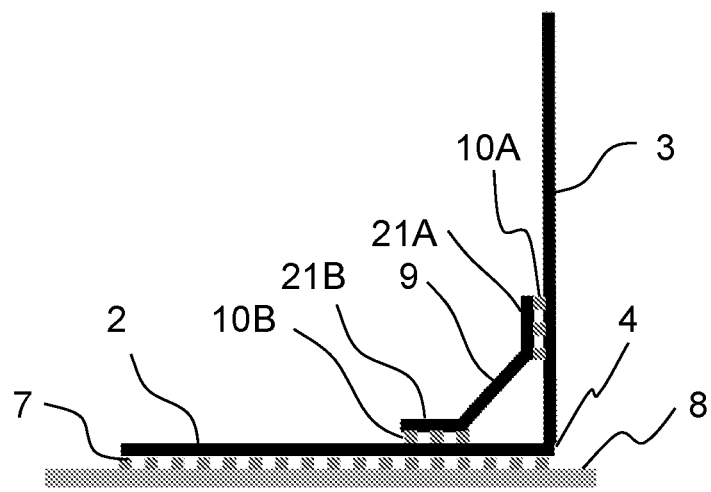
Figure 7:
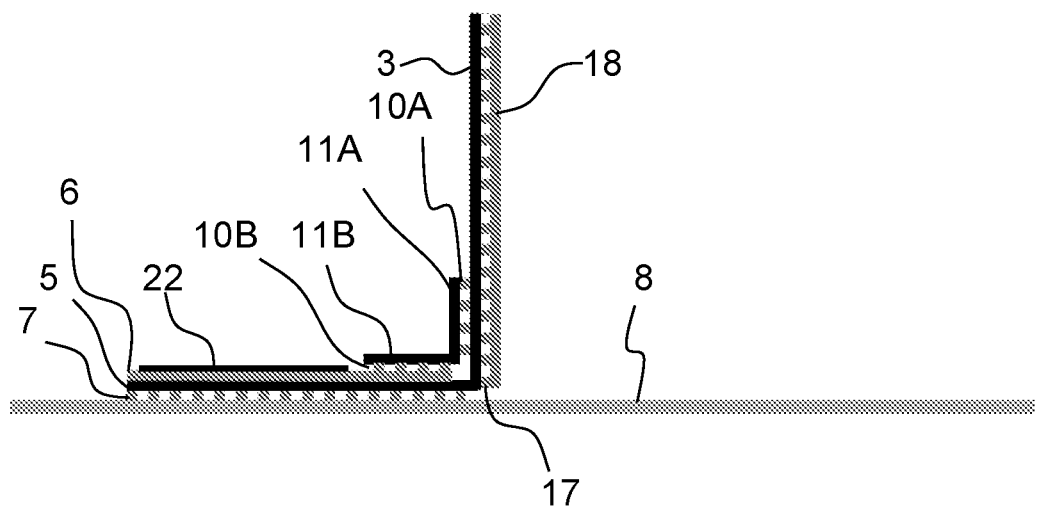

FIG. 4 is a sketch of the cover unit in straight transport condition and alternative use thereof in straight conditions a) before and b) after application to the skin of the patient, FIG. 5 is a sketch of the skin cover unit and use thereof in a) straight transport conditions but with the stabilizer already bent, and b) after application to the skin of the patient with the wall in bent condition relatively to the window;

FIG. 6 is a sketch of a further embodiment of a stabilizer;

FIG. 7 is a sketch similar to FIG. 5b with an added gel-removal strip;

FIG. 8 shows a) a sketch similar to FIG. 7 but with the gel-removal strip extending underneath the stabilizer for removal of the stabilizer together with the gel-removal strip, and b) shows the cover unit in flat condition after removal of the gel-removal strip and the stabilizer.

DETAILED DESCRIPTION/PREFERRED EMBODIMENT

Figure 1A:
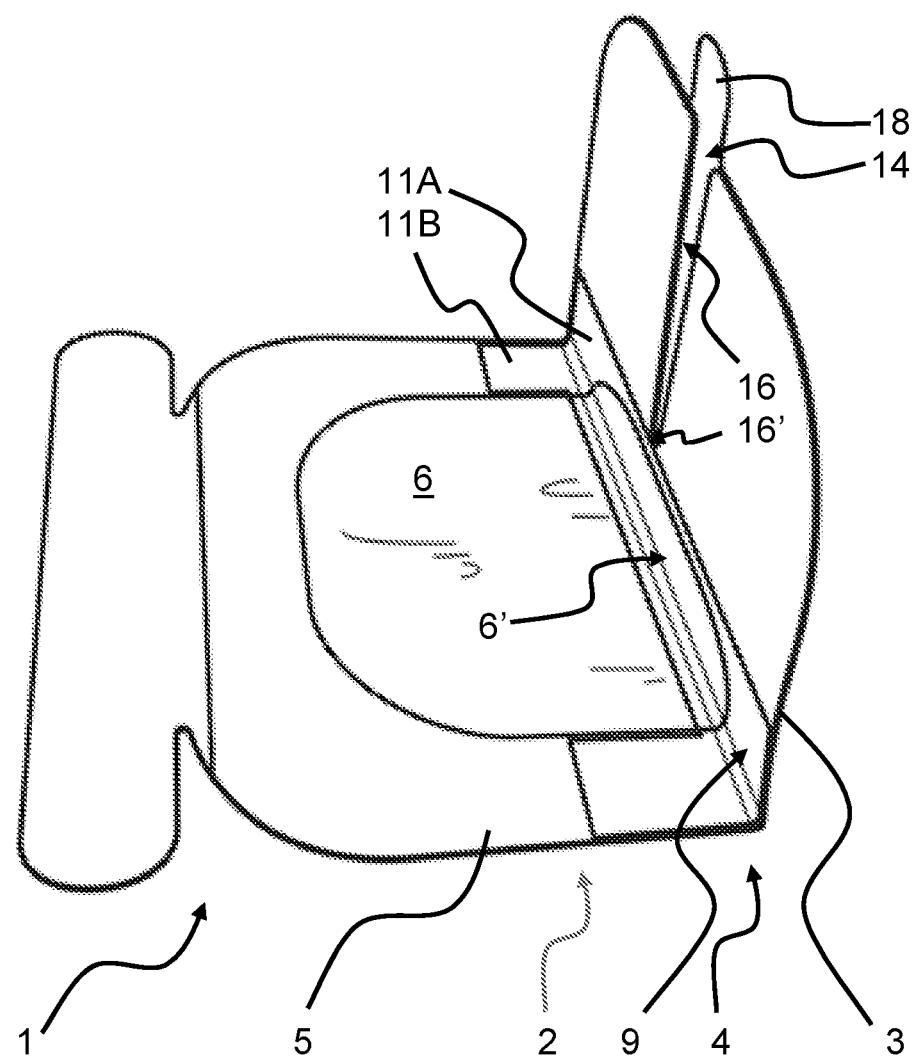
Figure 1B:
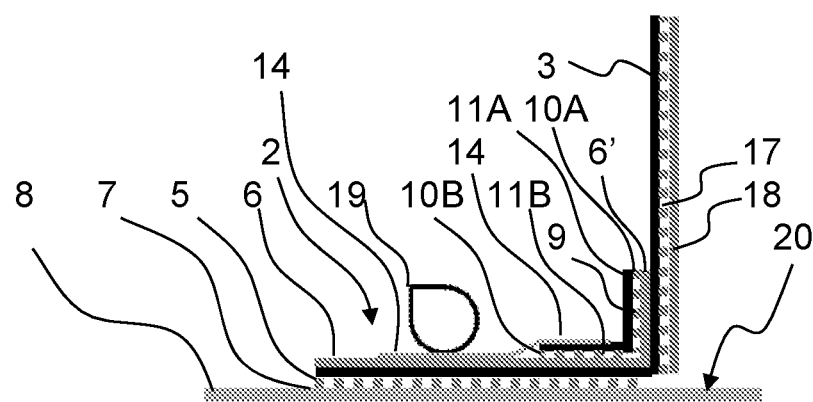
Figure 1C:
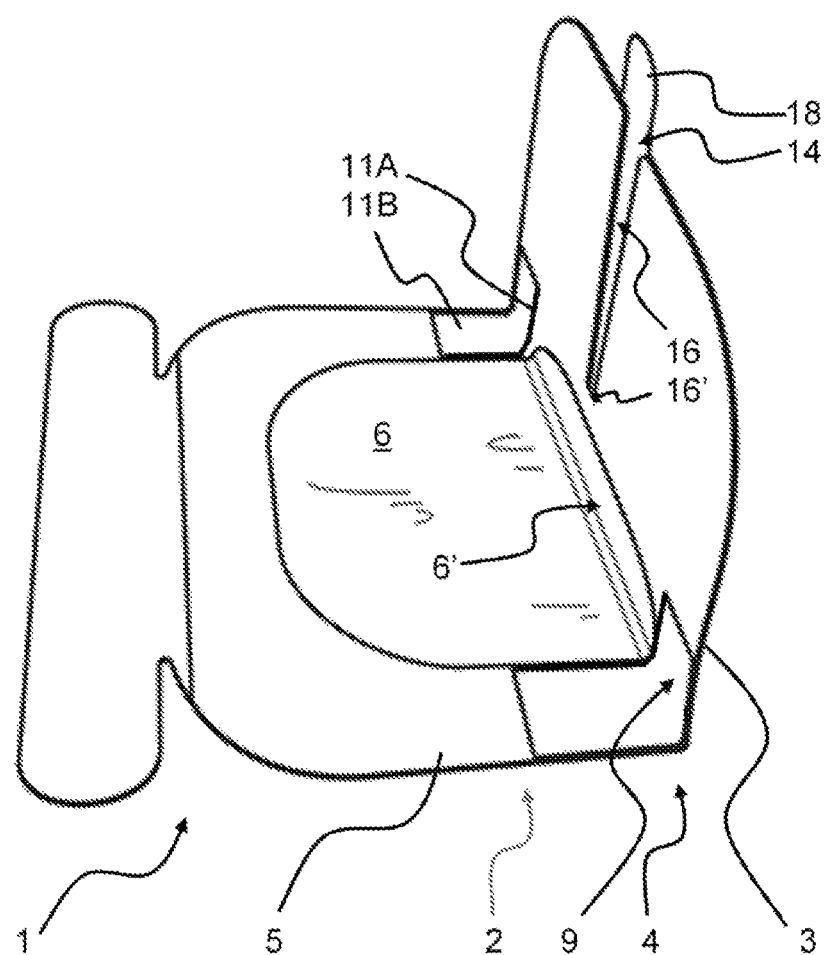

FIG. 1a and FIG. 1b are images of two alternative skin cover units 1 and FIG. 1c a principle sketch of the cover units 1. The cover unit 1 comprises a window 2 and a wall 3 in extension of the window 2. The wall 3 is connected to the window 2 by a bending region 4 for orienting the wall 3 into an angled orientation relatively to the window 2. The window 2 comprises a stabilizing frame 5 and an ultrasonic-transparent flexible sheet 6, typically polymer film, on or within the frame 5, or at least partially within the frame, for ultrasonic investigation of the insertion site 20 by an ultrasonic probe 19. The flexible sheet 6 is attached to and supported by the frame 5. Further, the flexible sheet 6 comprises an adhesive layer 7 on a first side of the flexible sheet 6 for gluing the window 2 onto the skin 8 of the patient.

In FIG. 1b, the flexible sheet 6 is shown as placed on the frame-side that is remote from the skin 8, however, it could alternatively be provided inside the frame 5 or between the frame 5 and the adhesive layer, facing the skin 8. If the flexible sheet 6 is placed on the frame 5 as illustrated in FIG. 1b, the frame 5 could also be provided with the adhesive layer 7 in order to glue the frame to the skin 8.

As a further alternative, only the frame 5 is provided with adhesive on the skin-adjacent side, and the flexible sheet is merely resting against the skin 8. Some polymer films are readily attaching to the skin even without glue and have sufficient ultrasonic transmission for the investigation.

The adhesive layer 7 as well as an ultrasonic-transmission fluid, typically gel 14, on top of the flexible sheet 6 provides a good contact for ultrasonic transmission from the probe 19 through the gel 14, through the flexible sheet 6, through the adhesive layer 7 and into the skin 8. This gel 14 is applied onto the flexible sheet 6 prior to the ultrasonic investigation and then removed again.

Furthermore, the skin cover 1 unit comprises a stabilizer 9, in or at the bending region 4. The stabilizer 9 is configured for maintaining the angled orientation between the wall 3 and the window 2 only by a stabilizing action of the stabilizer 9, for example when the skin cover unit 1 is positioned on top of a flat straight skin surface. In FIGS. 1a, 1b, and 1c, the stabilizer 9 is illustrated as an angled profile with two legs 11A, 11B, of which one leg 11A is glued with a first stabilizer-adhesive 10A to the wall 3 and the other leg 11B is glued with a second stabilizer-adhesive 10B to the window 2, thus maintaining the angled orientation between the wall 3 end the window 2. Typically, the flexible, ultrasonic transparent flexible sheet 6 is also light transparent in order for inspection by the eye and/or a camera.

In case that the flexible sheet 6 is provided on the upper side of the frame 5, which is the side remote from the side with the adhesive 7, the stabilizer 9 would be attached to the flexible sheet 6 on that portion of the flexible sheets that is itself attached to the frame. If the flexible sheet 6 is only provided within the frame 5, the stabilizer would be attached to the frame 5 directly, instead, as the frame at least partially surrounds the flexible sheet 6. The stabilizer 9 would be attached to the frame if the flexible sheet 6 is provided between the frame 5 and the skin 8, as the frame 8 in this case is attached to the opposite, upper side of the flexible sheet 6. In either case, the stabilizer is attached to the frame, either directly or through the film on the frame. Various embodiments and variations of the principle are possible.

The upstanding wall 3 is provided with a wall adhesive layer 17 covered by a cover sheet 18, the use of which is explained in more detail in the following, especially in connection with FIGS. 4 and 5.

The stabilizer 9, as illustrated in FIG. 1a, has a second leg 11B fastened to the frame 5 on either side of the frame 5. However, the leg 11A that is attached to the wall 3 stretches across the wall 3 from one side edge of the wall to the opposite side edge of the wall 3. The configuration of the stabilizer in this embodiment resembles a C-shape.

As illustrated in FIGS. 1a and 1b and 1c, the flexible sheet 6 extends around the bending region 4 with a minor part 6' of the flexible sheet 6 so that the minor part 6' is bent upwards together with the wall 2.

In the case of FIG. 1a, this implies that the stabilizer portion extends with its leg 11A across a portion of the wall 2 and extends partially along a perimeter of the sheet 6, covering the upwards bent minor part 6' of the sheet 6.

Alternatively, as illustrated in in FIG. 1c, the stabilizer 9 is provided as two separate bent strips, one on either side of the flexible sheet 6. Each strip has the first leg 11A attached to the wall and the second leg 11B attached to the frame 5 at the perimeter of the sheet 6 and outside the sheet 6, where the sheet 6 covers the ultrasonic-transparent part of the window 2.

However, this configuration of the bent sheet 6 is not necessary, and the flexible sheet 6 is illustrated in the following sketches as not extending around the bending region 4.

Figure 1D:
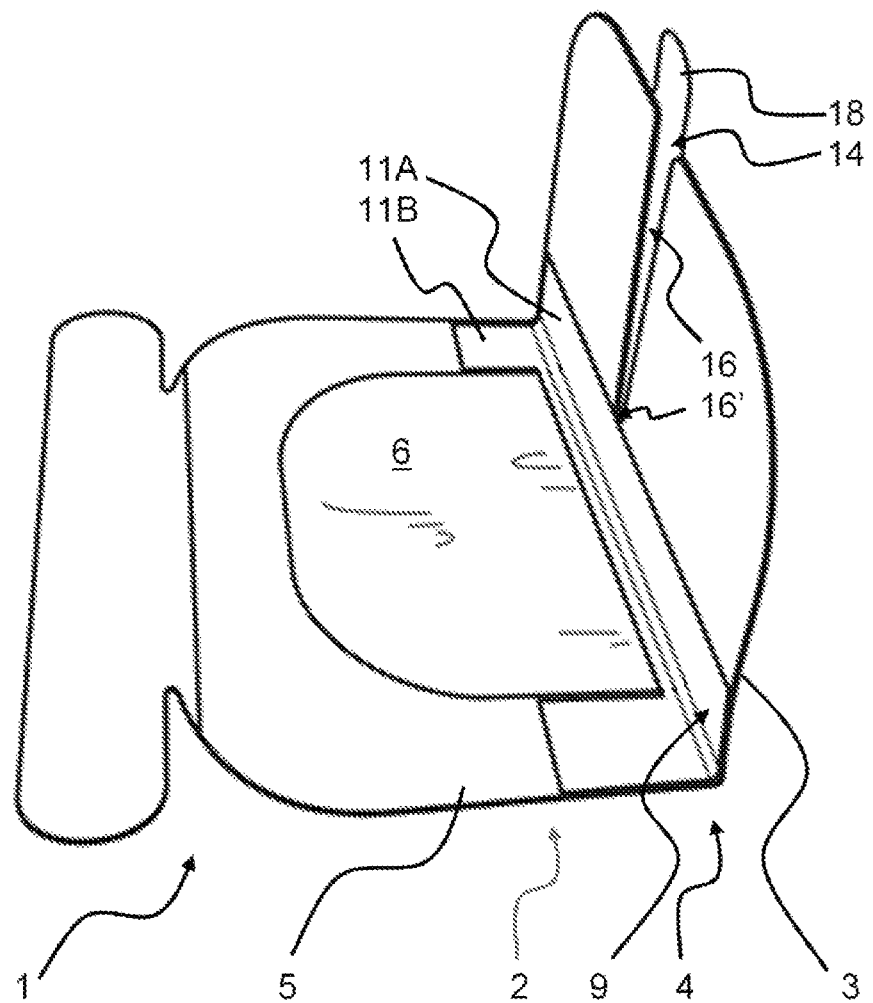

In an alternative embodiment of FIG. 1*d*, the sheet 6 is not bent upwards with the wall 2 but has a perimeter at the stabilizer 9 at the bending region 4. In this case, the sheet 6 is only provided flat against the skin.

As a further alternative, the configuration of the wall 3 and window 2 with a frame 5 of FIG. 1*d* can be combined with the stabilizer 9 strips of FIG. 1*c*.

In all cases of, the stabilizer 9 is outside that part of the window 2 that is used for ultrasonic investigation.

It should be mentioned that the stabilizer 9 can be attached to the window 2 and the wall 3 from the onset and then bent into an angled configuration, which is then maintained due to the non-resilient material of the stabilizer 9, for example metal.

Alternatively, one leg 11A of the stabilizer 9 is fastened to the wall 3 and the other leg 11B is not yet fastened to the window 2, or vice versa, but is only fastened to the window, or respectively the wall, once the orientation between the wall and the window has been adjusted. Options of this principle are explained in greater detail below.

Figure 2A:
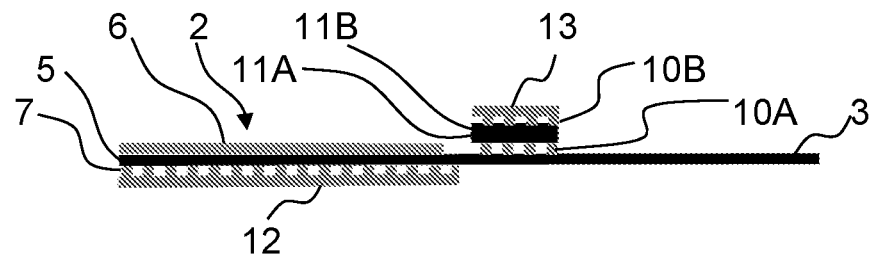
FIG. 2 illustrates the preparation procedure a) before bending the cover unit and b) after bending the stabilizer, and c) after bending the wall relatively to the window.
Figure 2B:
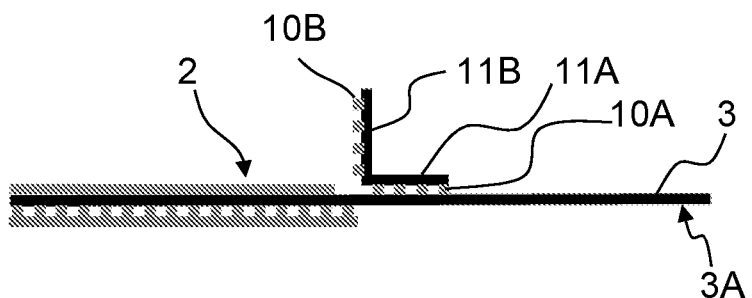
Figure 2C:
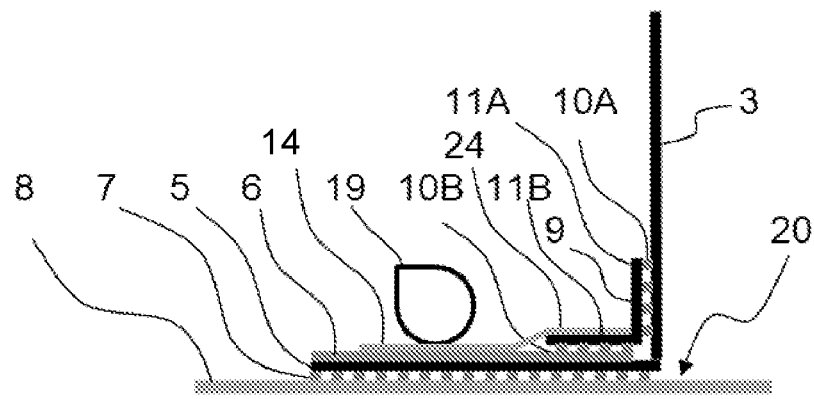

FIG. 2*a* illustrates a possible package and transport condition of the cover unit 1. The wall 3 is oriented in flat extension of the window 2. The adhesive layer 7 for gluing on the skin is covered by a removable cover sheet 12, typically a paper sheet. The two legs 11A and 11B of the stabilizer 9 are folded together, and configured for unfolding, as illustrated in FIG. 2*b*. The second stabilizer-adhesive 10B is covered by a further cover sheet 13, typically further paper sheet, which is removed from the second stabilizer-adhesive 10B, such as illustrated in FIG. 2*b*. Once, the cover unit as per FIG. 1 is removed from its package (not shown) and the further cover sheet 13 is removed from the second stabilizer-adhesive 10B, the wall 3 is bent about the bending region 4 into an angled orientation relatively to the window 2, and the second stabilizer-adhesive 10B is subsequently attached to the window 2, which stabilizes the orientation of the wall 3 relatively to the window 2. For attachment to the skin 8, the cover sheet 12 is removed, and the adhesive layer 7 of the window 2 is glued to the skin 8. This is preferably done before bending the wall 3 relatively to the window 2 but can also be done after bending the wall 3.

In some events, the cover unit 1 is removed from the patient after the ultrasonic investigation and insertion of a puncture device, especially a cannula insertion or, alternatively, insertion of other puncture device, for example electrode or probe. In other situations, the cover unit 1 remains on the skin 8 of the patient even after the investigation and insertion of the puncture device, for example cannula. In the latter case, the wall 3 can, in principle, be removed from the window 2, for example by cutting it off. Alternatively, the wall 3 is bent onto the window 2 and remains there. For these situations, the wall 3 does not need to be provided with adhesive 17 in contrast to the illustrations in FIG. 1*b* and the illustrations in FIGS. 4 and 5.

However as explained in more detail in the following, the wall 3 is optionally glued onto the skin 8 after the ultrasonic investigation and insertion of the cannula or other puncture device into the skin 8. Thus, although, the adhesive layer 7 is shown in FIG. 1*b* as only extending along the window 2, it is typically also provided under the wall 3. Such embodiments are illustrated in FIG. 1*b* and FIGS. 4 and 5 and described in more detail in the following.

Figure 3A:
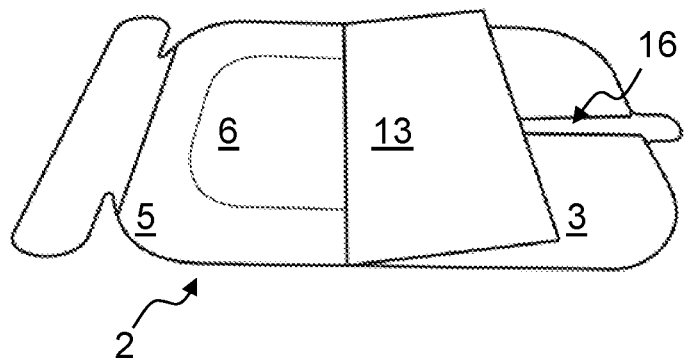
FIG. 3 shows images of the skin cover unit in flat straight condition a) before and b) during removal of a parts of the cover sheet and b) during bending and before final attachment of the stabilizer.
Figure 3B:
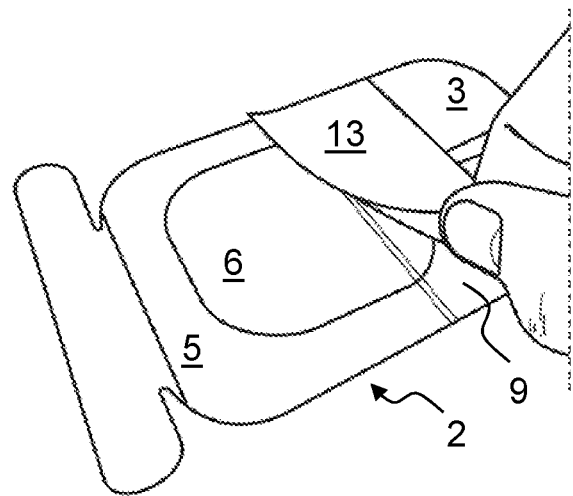
Figure 3C:
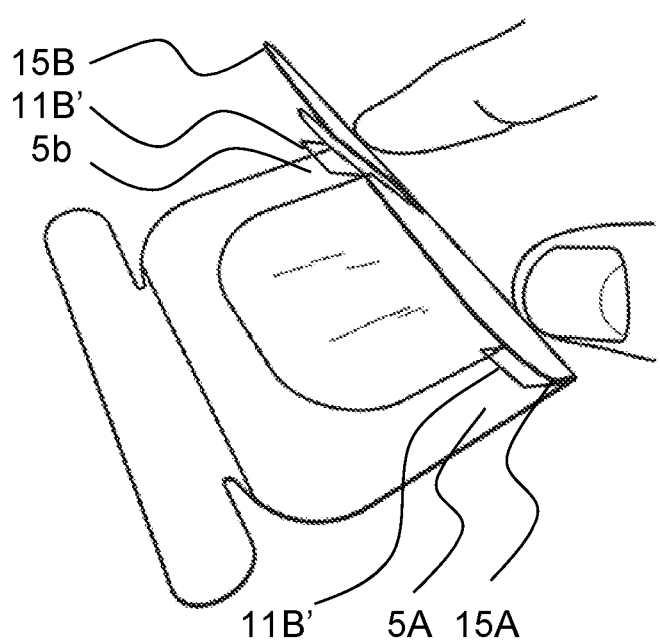

FIG. 3*a*, *b*, and *c* illustrate a sequence of preparatory steps from the just-unpackaged condition to the bent configuration. In FIG. 3*a*, the cover unit 1 is in flat, straight configuration just after unpacking. The wall 3 is in straight extension of the window 2. The window 2 is not yet transparent, as it is covered by a cover sheet (not shown) on its skin-adjacent side. However, once such cover sheet is removed, as illustrated in FIG. 3*b*, the transparent flexible sheet 6 is clearly visible inside the frame 5. The further cover sheet 13 is visible in FIG. 3*a*, and in the process of removal in FIG. 3*b*. After removal of the further cover sheet 13, two flaps 11B', corresponding to the second leg 11B of FIG. 1B, are visible in FIG. 3*c*. These two flaps 11B' are two portions of the stabilizer 9 and provided at each of two opposite edges 15A, 15B of the wall 3 for fastening the two flaps 11B' to two opposite parts 5A, 5B of the frame 5 of the window 2. Once, these flaps 11B' are glued onto the window 2, the wall 3 is fixed in orientation relatively to the window 2, as illustrated in FIG. 1*a*.

In order to provide multiple functions, the wall 3 is provided with a slot 16 that extends from an edge of the wall 3 towards the window 2. As best seen in FIG. 1*a*, the slot 16 has a bottom 16' which is near the bending region 4 and close to the flexible sheet 6.

As illustrated in the sketch of FIGS. 1*b*, 4*a*, 5*a* and 5*b*, the wall 3 comprises a first wall side 3A with an adhesive 17 which is covered by a wall cover sheet 18. Once, the wall cover sheet 18 is removed, the first side 3A of the wall 3 can also be glued to the skin 8 of the patient by the adhesive 17.

In the initial form, the adhesive 17 of the first wall side 3*a* is covered by a wall cover sheet 18 in order for the user to keep the wall cover sheet 18 on the adhesive 17 of the first wall side 3A while using the wall 3 in upstanding configuration, stabilized by the stabilizer 9, for safe ultrasonic investigation adjacent to the insertion site 19, as explained above and as illustrated in the FIG. 1*b* and FIG. 5*b*, while the wall 3 is bent in the bending region 4 relatively to the window 2.

The user can then select removing the wall cover sheet 18 from the adhesive 17 and gluing also the wall 3 to the patient's skin 8 after insertion of the puncture device, especially a cannula, into the skin 8, such that the puncture device 23, especially a cannula, is located inside the slot 16. For the latter case, the stabilizer 9 has to be deactivated, for example by cutting it or by partial detachment from the window 2 or the wall 3. In the embodiment with the stabilizer legs flaps 11B, these are decoupled from the window 2 or frame 3 or both for the de-activation. Alternatively, the stabilizer 9 is cut for de-activation.

As an alternative, the user can selectively glue the wall 3 as well as the window 2 to the skin 8 of the patient and insert the puncture device, especially a cannula, into the skin 8 through the slot 18 while performing the ultrasonic investigation with the probe 19 through the window 2. In this case, the cover unit 1 is used in straight condition and the wall 3 is not used in upstanding configuration.

Figure 4A:
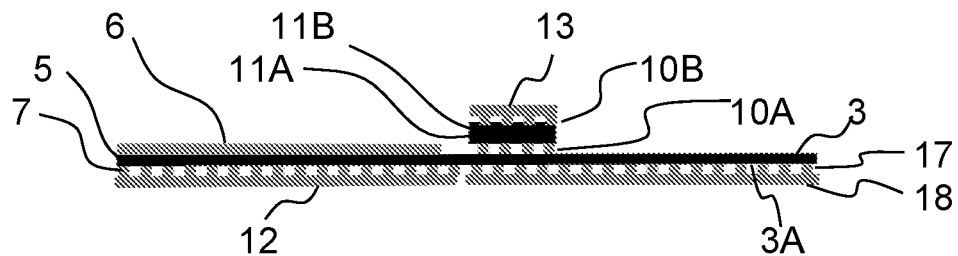
Figure 4B:

The flat configuration of the cover unit 1 with both the wall 3 and the window 2 being glued to the skin is illustrated in FIG. 4*b*. In this illustration, the stabilizer 9 has not been activated but remained in the transport condition.

When starting with the straight transport condition of the skin cover unit 1, as illustrated in FIG. 4*a*, the user has several options. As a first option, the user can remove the cover sheets 12 and 18 and glue the skin cover unit 1 onto the skin 8 of the user while the skin cover unit 1 is in straight condition, such as illustrated in FIG. 4*b*. As a second option, the user can remove the cover sheet 13 from the stabilizer 9 and bend the stabilizer 9 into the angled orientation, as illustrated in FIG. 5a and then raise the wall 3 into the upstanding configuration as in FIG. 5b and FIG. 1b. After ultrasonic investigation, the user may optionally lay down the wall 3 onto the skin 8, similar to the configuration of FIG. 4b.

In these ways, the cover unit 1 is has multiple functions. On the one hand, it preserves the function of the prior art and, on the other hand, it adds the function of the upstanding wall 3 which is stabilized by the stabilizer 9 in case that the skin 8 surface is flat.

FIG. 6 illustrates a further embodiment of a stabilizer 9. The stabilizer 9 is fastened to a first point or region 21A on the wall 3 and a second point or region 21B on the window 2, for example on the frame 5, where both points or regions 21A, 21B are remote from the bending region 4. The stabilizer 9 connects these two remote points or regions 21A, 21B, thus forming a stable triangular configuration between the two points or regions 21A, 21B and the bending region 4.

Although, the upstanding wall 3 is illustrated as having a perpendicular orientation relatively to the window 2, this is not strictly necessary, as the angle between the wall 3 and the window 2 can be adjusted to other angles, for example in the range of 45-135 degrees.

Optionally, in order to ease removal of the gel, a gel-removal strip 22, see FIG. 7, is provided on top of the flexible sheet 6. This gel-removal strip 22 is also ultrasonic-transparent and is taken off and removed from the ultrasonic-transparent flexible sheet 6 together with the gel such that wiping off the gel from the flexible sheet 6 is avoided.

Figure 8A:
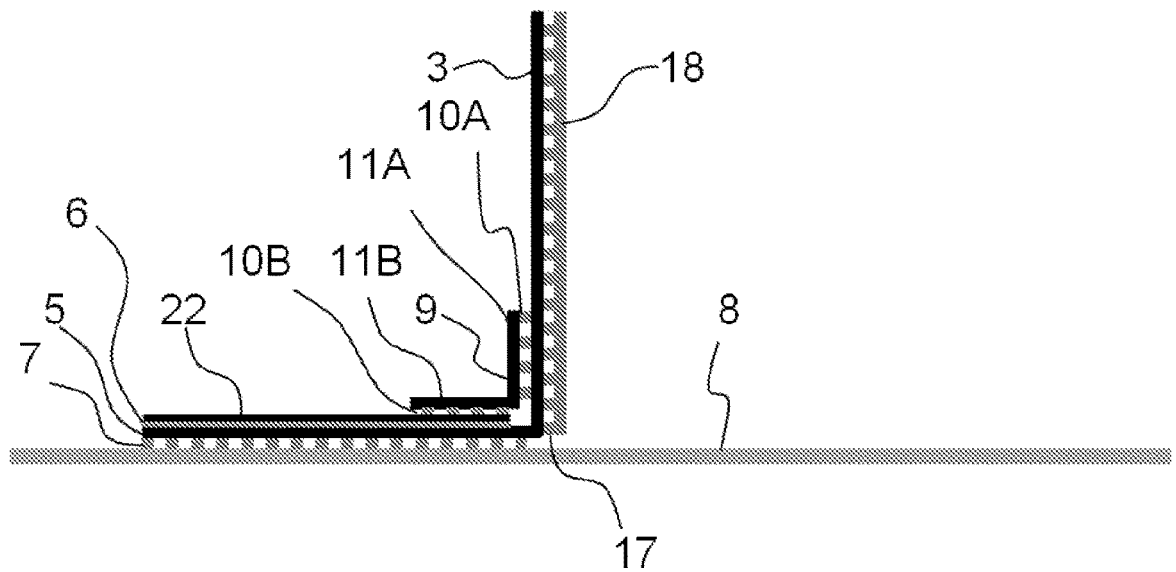
Figure 8B:
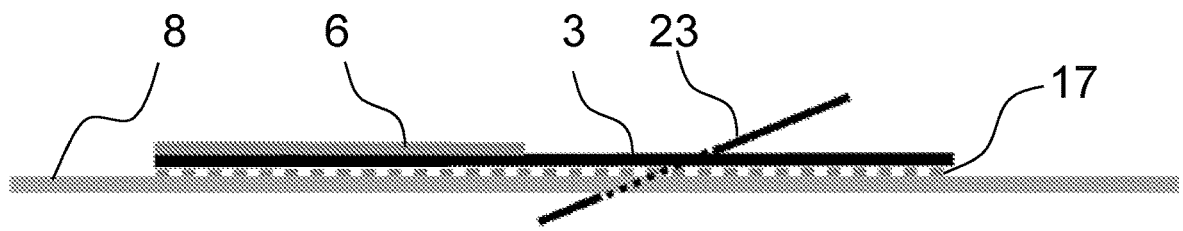

In FIG. 8a is a sketch similar to FIG. 7 but with the gel-removal strip 22 extending underneath the second leg 11B of the stabilizer 9 in order for the stabilizer 9 being removed together with the gel-removal strip 22 when the user pulls off the gel-removal strip 22 from the surface of the flexible sheet 6. For this, the adhesive 10A of the first leg 11A of the stabilizer 9 is pulled off the upstanding wall 3. Once the stabilizer 9 is removed, the upstanding wall 3 can be laid flat down on the skin 8 and glued to the skin 8 by the adhesive 17, once the wall cover sheet 18 for covering adhesive 17 has been removed. This situation is illustrated in FIG. 8b. The puncture device 23 then extends through the slot 16 and through the skin 8 into the underlying tissue.

It is pointed out that the gel-removal strip 22 could also extend underneath the adhesive 10A and first leg 11A of the stabilizer 9 a distance up the upstanding wall 3. In this case the gel-removal strip 22 extends entirely under the stabilizer 9 and endures that the entire stabilizer is removed together with the gel-removal strip 22.

REFERENCE NUMBERS 1 cover unit
2 window
3 wall
3A first wall side
4 bending region
5 stabilizing frame
5A, 5B opposite parts of frame
6 ultrasonic-transparent flexible sheet, typically polymer film, within the frame 5
7 adhesive layer
8 skin
9 stabilizer
10A, 10B first and second stabilizer-adhesive
11A, 11B first and second legs of bent profile as example of stabilizer 9
11B' flaps as two portions of the stabilizer 9
12 removable cover sheet, typically a paper sheet, covering adhesive layer 7
13 further cover sheet covering second stabilizer-adhesive 11B
14 gel
15A, 15B opposite edges of the wall 3
16 slot in wall 3
17 adhesive on first side 3A of the wall 3
18 wall cover sheet for covering adhesive 17
19 ultrasonic probe
20 insertion site
21 attachment regions of stabilizer 9
22 gel-removal strip
23 cannula or, optionally, other puncture device

The invention claimed is:

1. A surgical skin cover unit (1) for use when inserting a cannula or other puncture device (23) through the skin of a patient, wherein said skin cover unit (1) comprises a stabilizing frame (5), the frame comprising a window (2) and a wall (3), the wall (3) being provided in extension of the window (2) and connected to the window (2) by a bending region (4) for bending the bending region so that the wall (3) gets into an angled orientation relative to the window (2); wherein the window (2) comprises an adhesive layer (7) on a first side of the window (2) for gluing the window (2) onto the skin (8) of the patient; wherein the window (2) comprises an ultrasonic- transparent flexible sheet (6) for ultrasonic investigation of the patient through the flexible sheet from a second side of the window (2), which is opposite the first side of the window (2); wherein the skin cover unit (1) comprises a non-resiliently bendable stabilizer (9), wherein the stabilizer (9) is provided in or at the bending region (4) and is configured for maintaining the angled orientation between 45-135 degrees between the wall (3) and the window (2) by a stabilizing action of the stabilizer (9), wherein the stabilizer (9) comprises two legs, where each leg crosses the bending region and is fastened to the wall side of the frame and to the window side of the frame.

2. The surgical skin cover unit according to claim 1, wherein the stabilizer (9) is non-resiliently bendable and configured for adopting and maintaining a selectable bending condition when being bent for thereby maintaining a selected orientation of the wall (3) relative to the window (2).

3. The surgical skin cover unit according to claim 1, wherein the flexible sheet (6) is provided within the frame (5) and attached to and supported by the frame (5).

4. The surgical skin cover unit according to claim 1, wherein the wall (3) comprises a slot (16) extending from an edge of the wall (3) towards the window (2); and wherein the wall (3) comprises a first wall side (3A) with an adhesive (17) for also gluing the wall (3) to the skin (8) of the patient and for locating the cannula or other puncture device inside the slot (16) while the wall (3) is glued to the skin of the patient; wherein the adhesive (17) of the first wall side (3A) is covered by a wall cover sheet (18) for keeping the wall cover sheet (18) on the adhesive (17) of the first wall side (3A) while using the wall (3) as an upstanding wall (3) adjacent to an insertion site (20), while the wall (3) is in bent orientation relative to the window (2), and for selectively removing the wall cover sheet (18) from the adhesive (17) and gluing the wall (3) to the patient's skin (8) for locating the cannula or other puncture device within the slot (16) while the cannula or other puncture device is inserted in the skin (8).

5. The surgical skin cover unit according to claim 1, wherein the skin cover unit comprises a gel-removal strip (22) covering the flexible sheet (6) on the second side of the window (2) wherein removal of the gel-removal strip also removes potential gel (14) from the second side; wherein the gel-removal strip (22) extends under at least part of the stabilizer (9) wherein manual removal of the gel-removal strip (22) from the flexible sheet (6) also removes the stabilizer (9).

6. The skin cover unit according to claim 1 for separating the insertion site (20) of the cannula or other puncture device from the ultrasonic probe (19) on the skin of the patient.

7. A method for preparing an insertion site for a cannula or other puncture device (23) on a skin (8) of a patient, the method comprising providing a skin cover unit (1) comprising a window (2) and a wall (3), the window comprising a stabilizing frame (5) and the wall (3) being provided in extension of the window (2) and connected to the window (2) by a bending region (4) for bending the bending region so that the wall (3) gets into an angled orientation relative to the window (2); wherein the window (2) comprises an adhesive layer (7) on a first side of the window (2) for gluing the window (2) onto the skin (8) of the patient; wherein the window (2) comprises an ultrasonic-transparent flexible sheet (6) for ultrasonic investigation of the patient through the flexible sheet; wherein the method comprises gluing the first side of the window (2) onto the skin (8) of the patient and, before or after the gluing, bending the bending region (4) for changing the angled orientation of the wall (3) into an angle in the range of 45-135 degrees relatively relative to the window (2) and applying an ultrasonic probe (19) to the second side of the window (2) and ultrasonic-imaging the insertion site (20) for controlled insertion of the cannula or other puncture device (23) into the patient; wherein the skin cover unit (1) comprises a stabilizer (9), wherein the stabilizer (9) is provided in or at the bending region (4) and is configured for maintaining the angled orientation between the wall (3) and the window (2) by a stabilizing action of the stabilizer (9), wherein the method comprising, by the stabilizer (9) maintaining the angled orientation of the wall (3) relative to the window (2) in order for the wall (3) to separate the insertion site (20) from the window (2), wherein the stabilizer (9) is a bendable sheet comprising two legs, where each leg crosses the bending region and is fastened to the wall side of the frame and to the window side of the frame, wherein the method comprises bending the wall (3) relative to the window (2) at the bending region (4) into an angled orientation between the wall (3) and the window (2).

8. The method according to claim 7, wherein the stabilizer (9) is non- resiliently bendable and configured for adopting and maintaining a selectable bending condition when being bent for thereby maintaining a selected orientation of the wall (3) relative to the window (2), wherein the method comprises non-resiliently bending the stabilizer (9) into a selected bent configuration and by the stabilizer (9) maintaining the selected bent configuration.

9. The method according to claim 7, wherein the ultrasonic-transparent flexible sheet (6) is provided within the frame (5), the flexible sheet (6) being attached to and supported by the frame (5).

10. The method according to claim 7, wherein the wall (3) comprises a slot (16) extending from an edge of the wall (3) towards the window (2); and wherein the wall (3) comprises a first wall side (3A) with an adhesive (17) for also gluing the wall (3) to the skin (8) of the patient and for locating the cannula or other puncture device inside the slot (16) while the wall (3) is glued to the skin of the patient; wherein the adhesive (17) of the first wall side (3A) is covered by a wall cover sheet (18), and the method comprises keeping the wall cover sheet (18) on the adhesive (17) of the first wall side (3A) while using the wall (3) as an upstanding wall (3) adjacent to the insertion site (20), while the wall (3) is in a bent orientation relative to the window (2), and selectively removing the wall cover sheet (18) from the adhesive (17) and gluing the wall (3) to the patient's skin (8) for locating the cannula or other puncture device within the slot (16) while the cannula or other puncture device is inserted in the skin (8).

11. The method according to claim 7, wherein the surgical skin cover unit comprises a gel-removal strip (22) covering the flexible sheet (6) on the second side of the window (2) wherein removal of the gel-removal strip also removes potential gel (14) from the second side; wherein the gel-removal strip (22) extends under at least part of the stabilizer (9) and the method comprises manually removing the gel-removal strip (22) from the flexible sheet (6) wherein the manual removal also removes the stabilizer (9).

* * * * *